US008673564B2

(12) United States Patent
Simons

(10) Patent No.: US 8,673,564 B2
(45) Date of Patent: Mar. 18, 2014

(54) IN SITU METHODS FOR GENE MAPPING AND HAPLOTYPING

(75) Inventor: Malcolm James Simons, Victoria (AU)

(73) Assignee: Haplomic Technologies Pty Ltd, Victoria (AU)

( * ) Notice: Subject to any disclaimer, the term of this patent is extended or adjusted under 35 U.S.C. 154(b) by 306 days.

(21) Appl. No.: 12/663,188

(22) PCT Filed: Jun. 6, 2008

(86) PCT No.: PCT/AU2008/000808
§ 371 (c)(1),
(2), (4) Date: Feb. 5, 2010

(87) PCT Pub. No.: WO2008/148161
PCT Pub. Date: Dec. 11, 2008

(65) Prior Publication Data
US 2010/0173309 A1    Jul. 8, 2010

(30) Foreign Application Priority Data

Jun. 7, 2007    (AU) ................................ 2007903074

(51) Int. Cl.
*C12Q 1/68* (2006.01)

(52) U.S. Cl.
USPC .......................................... 435/6.11; 435/6.1

(58) Field of Classification Search
None
See application file for complete search history.

(56) References Cited

U.S. PATENT DOCUMENTS

| 7,300,755 | B1 * | 11/2007 | Petersdorf et al. | ........... | 435/6.16 |
| 7,563,572 | B2 * | 7/2009 | Pont-Kingdon et al. | ...... | 435/6.11 |
| 2004/0137470 | A1 | 7/2004 | Dhallan | | |
| 2004/0248144 | A1 * | 12/2004 | Mir | .................................. | 435/6 |
| 2007/0184457 | A1 * | 8/2007 | Pont-Kingdon et al. | ........... | 435/6 |
| 2008/0125324 | A1 * | 5/2008 | Petersdorf et al. | ................ | 506/1 |

FOREIGN PATENT DOCUMENTS

| WO | WO 99/28507 | 6/1999 |
| WO | WO 99/43851 | 9/1999 |
| WO | WO-2007022530 A2 | 2/2007 |
| WO | WO 2007/057647 A1 | 5/2007 |
| WO | WO 2007/062164 A2 | 5/2007 |

OTHER PUBLICATIONS

Hurley et al. Nucleic Acids Research. 2004. 32: e186 and supplemental material.*
Coriell Institute Catalog. Catalog ID GM17378 for DNA NA17378, printed on Feb. 28, 2012, available via URL: <ccr.coriell.org/Sections/Search/Search.aspx?PgId=165&q=NA17378>.*
Ersfeld, K. Methods in Molecular Biology. Ed. S.E. Melville (Humana Press Inc., Totowa, NJ) 2004. 27: 395-402).*
International Search Report for related International Patent Application No. PCT/AU2008/000808 completed Aug. 1, 2008.
Inazawa, J., et al., "Physical Ordering of Three Polymorphic DNA Markers Spanning the Regions Containing a Tumor Suppressor Gene of Renal Cell Carcinoma by Three-color Fluorescent in situ Hybridization," Jpn. J. Cancer. Res., vol. 83, pp. 1248-1252, (Dec. 1992).
Kwok, P., et al., "Single-Molecule Analysis for Molecular Haplotyping," Human Mutation, vol. 23, pp. 442-446, (2004).
Simons, M.J., et al., "HLA Haploid Typing of Single Diploid Individuals by Chromosome Microdissection (Haplo-Dissection)," Human Immunology, vol. 62, pp. S164, (2001).
Thalhammer, S., et al., "Generation of chromosome painting probes from single chromosomes by laser microdissection and linker-adaptor PCR," Chromosome Research, vol. 12, pp. 337-343, (2004).
Xiao, M., et al., "Determination of Haplotypes from Single DNA Molecules: A Method for Single-Molecule Barcoding," Human Mutation, vol. 0, pp. 1-9, (2007).
Zhang, K., et al., "Long-range polony haplotyping of individual human chromosome molecules," Nature Genetics, vol. 38, No. 3, pp. 382-387, (Mar. 2006).

* cited by examiner

*Primary Examiner* — Carla Myers
(74) *Attorney, Agent, or Firm* — Roberts, Mlotkowski, Safran & Cole, P.C.

(57) ABSTRACT

The present invention is directed to in situ methods for providing a definitive haplotype of a subject. The haplotype information generated by the methods described herein is more accurate than that provided by prior art methods that only give an inferred haplotype. Accordingly, in one aspect the present invention provides an in situ method for obtaining genetic information for a polyploid subject, the method including the steps of obtaining a biological sample from the subject, the sample containing: (i) at least one paternally-derived DNA molecule, and/or (ii) at least one maternally-derived DNA molecule, analyzing any one or more of the paternally- or maternally-derived DNA molecules for nucleotide sequence information, wherein the step of analyzing determines whether any two DNA markers are present in cis on one chromosome, or in trans across two sister chromosomes. Use of in situ methods such as FISH allows for the provision of phase-specific information on DNA markers without recourse to methods for physically separating sister chromosomes. Applicants propose that method eliminates the problem of incorrect or misleading inferences concerning the phase of two or more loci within a haplotype, and allows for revelation of two or more participatory genes within a haplotype, uncomplicated by differences in modes of inheritance.

8 Claims, No Drawings

IN SITU METHODS FOR GENE MAPPING AND HAPLOTYPING

CROSS-REFERENCE TO RELATED APPLICATIONS

This application is the National Phase of International Patent Application No. PCT/AU2008/000808, filed on Jun. 6, 2008, which claims the benefit of priority from Australia Patent Application No. 2007903074, filed on Jun. 7, 2007. The contents of these applications are incorporated herein by reference in their entirety.

The present invention relates broadly to the field of genetics. More specifically the invention relates to methods for genomic mapping, and methods for determining the haplotype of a subject using in situ methods.

BACKGROUND TO THE INVENTION

A genome map describes the order of genes or other markers and the spacing between them on each chromosome. Human genome maps are constructed on several different scales or levels of resolution. At the coarsest resolution are genetic linkage maps, which depict the relative chromosomal locations of DNA markers (genes and other identifiable DNA sequences) by their patterns of inheritance. A genetic linkage map shows the relative locations of specific DNA markers along the chromosome. Any inherited physical or molecular characteristic that differs among individuals and is detectable in the laboratory is a potential genetic marker. Markers can be expressed DNA regions (genes) or DNA segments that have no known coding function but whose inheritance pattern can be followed. DNA sequence differences are especially useful markers because they are plentiful and easy to characterize precisely.

Markers must be polymorphic to be useful in mapping; that is, alternative forms must exist among individuals so that they are detectable among different members in family studies. Polymorphisms are variations in DNA sequence that occur on average once every 300 to 500 bp. Variations within exon sequences can lead to observable changes, such as differences in eye color, blood type, and disease susceptibility. Most variations occur within introns and have little or no effect on the appearance or function of an organism, yet they are detectable at the DNA level and can be used as markers. Examples of these types of markers include (1) restriction fragment length polymorphisms (RFLPs), which reflect sequence variations in DNA sites that can be cleaved by DNA restriction enzymes, and (2) variable number of tandem repeat sequences, which are short repeated sequences that vary in the number of repeated units and, therefore, in length (a characteristic that is easily measured). The human genetic linkage map is constructed by observing how frequently two markers are inherited together.

Two markers located near each other on the same chromosome will tend to be passed together from parent to child. During the normal production of sperm and egg cells, DNA strands occasionally break and rejoin in different places on the same chromosome or on the other copy of the same chromosome (i.e., the homologous chromosome). This process (meiotic recombination) can result in the separation of two markers originally on the same chromosome. The closer the markers are to each other the more tightly linked the less likely a recombination event will fall between and separate them. Recombination frequency thus provides an estimate of the distance between two markers.

The value of the genetic map is that an inherited disease can be located on the map by following the inheritance of a DNA marker present in affected individuals (but absent in unaffected individuals), even though the molecular basis of the disease may not yet be understood nor the responsible gene identified. Genetic maps have been used to find the exact chromosomal location of several important disease genes, including cystic fibrosis, sickle cell disease, Tay-Sachs disease, fragile X syndrome, and myotonic dystrophy.

Current approaches to identifying genes influencing genic functions within a genome have two common characteristics: firstly, non-coding sequence-variant markers are employed to reveal chromosomal regions containing candidate genes; and secondly, genome-wide analyses seek associations between sequence-variant markers and a phenotype of interest. Gene discovery by genome-wide association analysis, also known as linkage disequilibrium mapping, is the subject of U.S. Pat. No. 5,851,762.

While genomic information is useful in linkage studies, information on the haplome is considered more useful for identifying markers of genomic regions of interest in defining disease-associated gene function. The use of haplomic sequences reduces error in linkage studies because there is no need to consider the involvement of second copy of the gene (as provided on the homologous chromosome) with the trait under consideration.

In 2003, a National Institutes of Health-funded international consortium commenced a three year, US$100,000,000 project to create a human genome haplotype map (termed the "HapMap") in order to facilitate gene discovery by haplotype-based, marker allele-disease gene association in complex diseases. This strategy of linkage disequilibrium allele-association mapping ('association mapping') involves unrelated, individual patients, and is the more recent alternative to the traditional approach of family (pedigree) linkage analysis when families are not available.

An assumption upon which HapMap is based is that haplotype inference from genotyping diploid DNA is sufficiently resolving for association mapping to warrant continuation as the strategy for genome-wide gene discovery.

A further assumption is that analysis of SNPs (single nucleotide polymorphisms) of a few hundred individuals from 4 populations (West African Nigerians, Japanese, Chinese, American) will be adequate to identify redundant SNPs, and thereby to identify haplotype-marking single SNPs, or minimum sets of SNPs, sufficient to characterize haplotype blocks in all, including admixed, populations. The HapMap consortium also proposes that only common haplotypes (>5-10%) will be important in common, multigenic diseases and in drug reactivity, and that these common haplotypes will be identifiable in a study of around 200 individuals.

A further assumption is that that the haplome is organized into discrete "blocks" with each block being identifiable with a unique SNP "tag". It is currently accepted in the field of genetics that use of the minimum essential SNPs revealed by the HapMap project will identify sufficient common haplotypes in any population for detection of excess haplotype sharing in disease-gene searches and drug-affective pharmacogenomics.

Thus, the present state of the art is that the HapMap will be definitive, and capable of providing more than sufficient information for linkage studies. However, closer inspection of the HapMap project suggests that the project will achieve only limited information at best, and may be fundamentally flawed in its application to multi-genic disease discovery. For example, SNP identification will detect only a proportion of extant haplotypes, perhaps not even all commonly occurring haplotypes. Uncommon haplotypes (that may not be detectable in the HapMap) may also contribute to genic functional differences between individuals.

The assumed block structure of the haplome may also lead to errors. Recombinations and other rearrangements can be expected to affect haplotype block structure in admixed populations that may not be revealed by a limited analysis of 'core' populations.

The resolving power of inferred haplotypes can be expected to be challenged where two or more genes, having different modes of inheritance (recessive, dominant, co-dominant), differing functions (disease-predisposing, disease-protective), acting at different stages of disease progression, occur within a single chromosomal region. Resolving power will be most challenged when risk is contributed by both chromosomes as in compound heterozygous recessive diseases, and where trans as well as cis co-dominant interactions occur with co-dominant inherited genes such as those of the HLA complex. The significance of these doubts has not been recognized in the art.

A critical test of the utility of haplotyping association mapping is the ability to identify genic regions of interest already identified by pedigree linkage analyses. In an important test case, association mapping failed to identify the 6p21.3 (HLA) region of genetic risk (RR: lower bound 20-upper bound infinity) in nasopharyngeal carcinoma identified by haplotype sharing linkage analysis. This points to another problem in the art: non-coding based strategies have insufficient resolving power to detect even the strongest genetic association with any common human cancer.

Many diseases are known or suspected to be multigenic. Indeed, it is thought that most diseases are multigenic, and that monogenic diseases are the exception. The identification of genes with involvement in multigenic diseases is complicated in the methods of the prior art due to the patterns of inheritance of the genes from the maternal and paternal genotypes. Thus, while the prior art methods of mapping and gene discovery have been useful in identifying genes having simple modes of inheritance and simple involvement in disease, there remains a clear need for more powerful methods to unravel gene involvement in complex diseases.

It is advantageous to provide alternative methods to investigate the haploid state of a cell. Where a given method is unsuitable for reasons of economy, ease of use, accuracy, availability of equipment or any other reason, an alternative method is available.

Accordingly, it is an aspect of the present invention to overcome or at least alleviate a problem of the prior art. In particular, the present invention aims to provide alternative methods for more accurately mapping a gene using haploid information The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is directed to in situ methods for providing inter alia a definitive haplotype of a subject. The haplotype information generated by the methods described herein is more accurate than that provided by prior art methods that only provide an inferred haplotype. Accordingly, in one aspect the present invention provides an in situ method for obtaining genetic information for a polyploid subject, the method including the steps of obtaining a biological sample from the subject, the sample containing: (i) at least one paternally-derived DNA molecule, and/or (ii) at least one maternally-derived DNA molecule, analyzing any one or more of the paternally- or maternally-derived DNA molecules for nucleotide sequence information, wherein the step of analyzing determines whether any two DNA markers are present in cis on one chromosome, or in trans across two sister chromosomes.

Applicant proposes that the use of an in situ method as described herein eliminates the problem of incorrect or misleading inferences concerning the phase of two or more loci within a haplotype, and allows for revelation of two or more participatory genes within a haplotype, uncomplicated by differences in modes of inheritance. The guarantee of strictly cis-phase associations is provided in the present methods by the selective analysis of maternally-derived DNA and paternally-derived DNA by an in situ method. Use of an in situ method allows for convenient analysis in the context of a general pathology or research laboratory.

In one form of the method the sequence information relates to an allele. In another form of the method the allele is a coding sequence allele.

Applicant recognizes the importance of problems inherent in the indiscriminate use of diploid material in combination with the use of maximum likelihood algorithms in defining a haplotype. It is anticipated that the errors in the methods of the prior art become particularly problematic when investigating traits that have a multi-genic basis.

The in situ analysis of a diploid genome or portion thereof may be performed on a diploid cell, such as a somatic cell. The use of naturally haploid material such as sperm cells or ova is to be avoided due to problems with obtaining these sex cells in the clinic. The avoidance of gametes in haplotyping has a further advantage when it is considered that the process of meiosis there are sometimes recombination events such that loci that were formerly linked in cis, become associated in trans. Thus, analysing a haplotype of a gamete will give different (i.e. incorrect) haplotype information to that of a haploid element obtained from a diploid cell.

In another aspect the present invention provides for the use of an in situ method as described herein for determining a definitive haplotype of a subject.

In another aspect the present invention provides a method for identifying a gene involved in a multi-genic disease or trait, the method including use of a method described herein. The provision of a definitive haplotype as provided by an in situ method described herein removes uncertainties that confound elucidation of the involvement of a single gene in a multi-genic system.

DETAILED DESCRIPTION OF THE INVENTION

In one aspect the present invention provides an in situ method for obtaining genetic information for a polyploid subject, the method including the steps of obtaining a biological sample from the subject, the sample containing: (i) at least one paternally-derived DNA molecule, and/or (ii) at least one maternally-derived DNA molecule, analyzing any one or more of the paternally- or maternally-derived DNA molecules for nucleotide sequence information, wherein the step of analyzing determines whether any two DNA markers are present in cis on one chromosome, or in trans across two sister chromosomes.

Applicant proposes that the use of an in situ method as described above eliminates the problem of incorrect or misleading inferences concerning the phase of two or more loci within a haplotype, and allows for revelation of two or more participatory genes within a haplotype, uncomplicated by differences in modes of inheritance. Furthermore, the method is amenable to incorporation into a general pathology or research laboratory.

The present invention is predicated at least in part on an improvement over the methods for haplotyping in the prior art, and definitive haplotyping methods described herein. In order to better understand the distinction it is instructive to consider the concept of the haplotype as it is presently understood in the art, and methods for determining the haplotype of a subject.

The term "haplotype" is a contraction of the phrase "haploid genotype", and is presently accepted to mean a set of nucleotide sequence polymorphisms or alleles present on a single maternal or paternal chromosome, usually inherited as a unit. In the case of a diploid organism such as a human, the haplotype will contain one member of the pair of alleles for a locus.

In the methods of the prior art, determination of a haplotype begins with the use of diploid material that is convenient to obtain clinically. Applicant proposes that the accepted forms of haplotyping indiscriminately using diploid material are inadequate. An alternative is to use naturally haploid material (from sperm or ovum for example) however this is generally inconvenient, and for females is overly invasive. Furthermore, sequence information from gametes can be confounded by crossing over events during meiosis such that cis-phase associations between SNPs cannot be assured to be authentic.

Since approaches of the prior art utilizing diploid DNA do not allow direct determination of loci linked in cis as haplotypes, occurrence probability of haplotypes is inferred by maximum likelihood and similar algorithm-based estimates. Thus there is always the possibility that two polymorphisms are present in trans phase, and therefore have not been inherited as a single Mendelian unit. The methods of the prior art are therefore more correctly described as providing an "inferred haplotype". The present methods relate more closely to the strict definition of haplotype by considering the fundamental unit of Mendelian inheritance as a chromosomal segment bounded by sites of parental recombination.

Hitherto, persons skilled in the art have not questioned the effect of errors introduced by failing to consider the potentially adverse result of indiscriminately using diploid starting material. The problems in determining trait associations in populations, or in haplotyping a subject have therefore not been recognized. By contrast, Applicant recognizes the importance of problems inherent in the indiscriminate use diploid material in combination with the use of maximum likelihood algorithms in defining a haplotype. It is anticipated that the errors in the methods of the prior art become particularly problematic when investigating traits that have a multigenic basis.

Thus, in one embodiment the present invention is directed to methods for providing genetic information in the form of a definitive haplotype. As used herein, the term "definitive haplotype" is intended to mean that strictly only cis-phase associations are considered in ascribing a haplotype. The methods described herein do not involve any estimation or inference as to whether two polymorphisms are present on the same molecule of DNA. This is different to the "inferred haplotype" of the prior art described above which is obtained by interrogating diploid material for sequence information (as performed in the HapMap project), without any regard to phase.

Quite apart from the problems of inference, the indiscriminate use of diploid cells introduces further complications arising from short allele dominance ("allele dropout") where the larger allele fails to specifically amplify. Thus, the presence of the larger allele is completely ignored, and erroneous haplotype information results.

The guarantee of strictly cis-phase associations in determining a haplotype is provided in the present methods by the selective analysis of paternally-derived DNA and/or maternally derived DNA for sequence information.

The in situ method may be carried out on the genome of a subject or portion thereof. As used herein the term "genome" means the total genetic material of a subject and includes a complete set of DNA sequences of the subject. Reference to a "portion thereof" of a genome means a portion of nucleic acid, such as DNA, from the genome of a subject.

The genome or portion thereof can be obtained from any cell or biological sample containing nucleic acid. Where the genome is obtained from a diploid cell, the cell may be induced into metaphase by the addition of inducing agents well known to the person skilled in the art such as colcemid. Discrete chromosomes appear at metaphase and are able to be dissected into constituent haplomic elements as described below.

The method is typically performed on an autosomal chromosome of a somatic cell. The term "autosomal chromosome" means any chromosome within a normal somatic or germ cell except the sex chromosomes. For example, in humans chromosomes 1 to 22 are autosomal chromosomes.

As discussed supra the use of naturally haploid material such as a sperm cell or ovum is to be avoided due to problems with obtaining these sex cells in the clinic. The avoidance of gametes in haplotyping has a further advantage when it is considered that during the process of meiosis there are sometimes recombination events such that loci that were formerly linked in cis, become associated in trans. Thus, analysing a haplotype of a gamete will give different (i.e. incorrect) haplotype information to that obtained from a diploid cell.

As used herein, the term "in situ method" is intended to include any method that does not require the physical isolation of a paternally-derived DNA from a maternally-derived DNA, or vice versa. An in situ method is capable of selectively analysing paternally-derived DNA in the presence of maternally-derived DNA and vice versa such that the phase of any two markers can be determined. In practical terms, the method used in the context of the present invention may be any method whereby a DNA molecule can be probed for predetermined markers, such that the binding of the probe can be shown to occur with one or both of any given pair of sister chromosomes. In this way, the method is capable of demonstrating that two DNA markers are present in cis (on one chromosome) or in trans (split across two sister chromosomes) where the two sister chromosomes have not previously been physically separated.

An advantage of an in situ method is that it is more easily incorporated into a standard pathology or research laboratory. Methods requiring, for example, physical separation of paternally- and maternally-derived chromosomes require the use of expensive and equipment such as micro-manipulators and laser catapulting microscopes. By contrast, an in situ method can be implemented using standard equipment and techniques such as fluorescence microscopy.

The skilled person will understand that an in situ method capable of providing phase-specific nucleotide sequence information could be implemented in a number of ways.

Accordingly, the present invention is not limited to any specific technique, and the following methods are to be considered only as illustrative.

In one form of the invention, the method is implemented using a fluorescence in situ hybridisation (FISH) technique. FISH refers to the use of labeled nucleic acid sequence probes for the visualization of specific DNA or RNA sequences on mitotic chromosome preparations or in interphase cells. One methodology for labeling a nucleic acid probe, be it DNA or RNA, is enzymatically via either random priming or nick translation incorporation of a fluorescent molecule- or immunogenic hapten-conjugated nucleotide analog. Direct chemical labeling can also provide probes useful in the context of the present invention. More recently peptide nucleic acid (PNA) molecules have been developed, and these can also serve as useful probes.

The hybridization target can be either RNA or denatured, single-stranded DNA. Once the probe has been given sufficient time to anneal to its complimentary target sequence, excess probe molecules are washed away and the hybridization pattern is visualized with a fluorescence microscope. Of note, hapten-labeled probes require detected with fluorescent-conjugated antibodies. Signal amplification techniques, such as the use of tyramides or rolling circle amplification, have been developed to increase signal intensities derived from small DNA targets previously undetectable by traditional approaches.

The probe for a FISH technique may be an oligonucleotide, a plasmid, a PNA, a cosmid, a YAC, a BAC or a library probe. In one embodiment, the probe is a PNA. Methods for PNA-FISH are disclosed in Strauss 2002 ("PNA-FISH" in FISH Technology. Rautenstrauss/Liehr Eds. Springer Verlag. Heidelberg).

Technically the ideal probes especially for interphase FISH should give strong, specific signals with little or no background and should have a high hybridization efficiency of greater than about 90%. Preferably, probes directed to the detection of SNPs are used.

Standard methods for implementing FISH techniques are know in the art. A basic FISH method may include the following steps:

Slides Preparation
1) Clean slides with 70% ethanol (to remove any grease or dust).
2) Place a few drops of pellet and let the slide air dry.
3) Place the slide in an incubator at 90° C. for one hour and a half to age, or at 37° C. overnight.

Slides Treatment
1) After 1.5 hours in the incubator, let the slide cool and then add 150-200 µl of 0.005% Pepsin/0.001M HCl and place them at 37° C. for 15 min.
2) Place in a coplin jar with PBS 1× for 5 min.
3) 5 min in post fixation wash
4) 5 min in Paraformaldehyde/PBS wash
5) 5 min in PBS 1×
6) 5 min each in ethanol series: 70%, 90%, 100% (slides can be left in 100% ethanol until ready to be hybridized).
7) Before hybridization with probe, slides are taken out and let air dry completely.

Direct Labelling of Probe by Nick Translation.
10 ul DNA
3 ul Buffer 10×
0.6 ul dAGC (for dUTP/CY-3, red) or 1.8 ul dAGT (for FluorX-dCTP, green)
0.3 ul dUTP/CY-3 or 0.9 ul for FluorX-dCTP
3 ul B-mercaptoethanol
0.3 ul DNApolymerase
6 ul DNAse (1:700 ul H2O)
$H_2O$ to reach 30 ul final volume
1) After preparing the labelling mixtures with enzymes and DNA, place it in a water bath at 16° C. for 2 hours.
2) After 2 hours, to precipitate the probe take the appropriate quantity of labelled probe and place it in a new eppendorf (say, 30 ul)
3) Add to the labelled probe:
3 µl Salmon Sperm DNA (SSD)
10 µl Cot-1 DNA (10 µl of Cot per 30 µl of labelled DNA, so for a cosmid add 15 µl)
1/10 Vol NaAC
3 Vol cold EtOH 100%

Precipitation
1) To precipitate, place eppendorf at −80° C. for 15 min, or at −20° C. for at least 30 min.
2) Centrifuge at +4° C. for 20 min.
3) Take supernatant off and dry the pellet
4) Resuspend pellet in Hybridization Mix
5) Place in thermomixer at room temperature for 10 minutes to mix.
6) Place probes on dried slides
7) Place coverslip and seal with rubber cement.
8) Place slides in Hybrite (Vysis) and start cycle Hybrite temperatures: Melt: 69° C. for 2 min (human slide) Hyb: 37° C. Overnight Co-Hybridization
Two probes are labelled with different fluorochromes and hybridized on the same slide: CY3-dUTP(red) and FluorX-dCTP (green). They can be easily used because they are both direct labelled probes.

Each probe is labelled individually, and then mixed together and precipitated. Example: 30 ul labelled probe A plus 30 ul labelled probe B plus 3 ul SSD plus (10 ul plus 10 ul) 20 ul Cot-1 DNA plus 8.3 ul NaAc plus 270 ul EtOH.

Post-Hybridization Washes
3 washes at 57° C. in 0.1×SSC for 5 min each
5 min in DAPI (60 ml of 2×SSC, 120 ul DAPI)
Add a few drops of Antifade DABCO on the coverslip and make sure there are no air bubbles between slide and coverslip Analysis
Analyse with LEICA DMRXA Fluorescent microscope. Images can be acquired using applied spectral imaging (ASI) camera and analyzed with FISH view 2.0 software The skilled person will be capable of modifying the protocol above for any specific application.

In the context of the present invention, a FISH probe directed to two markers on a chromosome (e.g., two SNPs) could be used to stain a metaphase spread from an autosomal cell of a subject. It may be found that one phenotype is noted where the two markers are present on a single chromosome (in cis), or present across two sister chromosomes (in trans). Using fluorescence microscopy, the two relevant sister chromosomes are identified. If the two probes bind to a single chromosome, then the markers are present in cis. If they bind to different chromosomes (one paternal and one maternal) then the markers are present in trans. It will be noted from this example, that it is not necessary to know which marker is on which chromosome. It is simply necessary to decide whether they are present on a single chromosome (irrespective of whether that chromosome is paternally-derived or maternally-derived) or distributed across the two sister chromosomes (i.e. one paternal and one maternal).

FISH methods may also be used in the context of a microarray platform for high throughput processing. DNA microarrays allow for simultaneous analysis of thousands of samples.

Another in situ technique suitable for implementing the present methods is primed in situ labelling. This technique is an alternative to FISH and is basically a single-cycle PCR reaction, requiring a single specific primer and labelled dUTP/dNTP solution. Typically the PRINS technique uses a specific primer, dNTPs with Dig-11-dUTP and DNA polymerase to perform a primer extension reaction on a chromosome preparation. PRINS reaction kits are available from Boehringer Mannheim. An exemplary protocol is described below.

Reaction Mixture
10×labeling buffer–3.0 ul
10×reaction solution–3.0 ul
primer–60~200 pmol
Taq DNA polymerase 3.0 ul (3 u)
ddH2O to 30 µl The reaction mixture is applied to a slide preparation and covered with a cover slip which is sealed in place with rubber cement. After the rubber cement has dried, the slide is placed onto a PCR block (a Hybaid Omni Gene in-situ Block).

Primer Extension

Primer extension occurs by one cycle of 93° C. for 5 minutes (to denature chromosomal DNA) followed by 61° C. for 30 minutes (for primer annealing and extension).

Detection of Signal

Carefully remove the rubber cement and cover slip, and stop the extension reaction by gently flooding the slide with 50 mM NaCl, 50 mM EDTA at 60° C. for 3 minutes. Signal detection follows the technique Hirai, H. and LoVerde, P. T. (1995) "FISH techniques for constructing physical maps on Schistosome Chromosomes." Parasitology Today 11(8), 310-314. Briefly:

1) Immerse in 50 ml of BN buffer (0.1 M sodium bicarbonate, 0.1% Nonidet P-40) for 10 minutes.
2) Immerse in 50 ml of blocking buffer (5% nonfat milk in BN buffer) for 10 minutes
3) Immerse in 50 ml of anti-digoxigenin-fluorescein conjugate (Boehringer Mannheim) (800 ng in blocking buffer) and incubate at 37° C. for 30 minutes in the dark.
4) Wash with excess BN buffer on a shaker at room temperature to remove unbound conjugate
5) Mount in 20 µl of anti-fade solution containing propidium iodide (30 ng/ml) and DAPI (30 ng/ml) to counterstain the chromosomes
6) Cover with a cover slip, remove excess mountant and observe.

It will be understood that the term "nucleotide sequence information" as used herein is intended to include information relating to two or more markers on a chromosome. A marker may be a single nucleotides (for example a SNP), or multiple contiguous nucleotides, or multiple discontinuous nucleotides.

Reference to "obtaining sequence information" is intended to include any in situ method known to the skilled artisan for determining the nucleotide sequence of a nucleic acid molecule. As used herein, the term "nucleic acid" encompasses either or both strands of a double stranded nucleic acid molecule and includes any fragment or portion of an intact nucleic acid molecule. Both DNA and RNA are included. For example: sequence information may be obtained by the binding (or lack of binding) of an informative oligonucleotide probe. Obtaining sequence information typically involves identification of SNPs, and the skilled person will be capable of designing probes capable of detecting any SNP. Typically, a probe will be around 25 nucleotides in length, with the polymorphic site designed to hybridise with the centre of the probe.

DNA can be obtained from virtually any tissue source (other than pure red blood cells). For example, convenient tissue samples include whole blood, semen, saliva, tears, urine, fecal material, sweat, buccal, skin and hair.

Methods involving the amplification of DNA (such as PCR) may be used in the context of the present invention. For example, primers specific for maternally-derived DNA or paternally-derived DNA may be used to selectively amplify regions of either or both of a sister chromosome pair. The PCR products are then sequenced to provide information on the region(s) with the knowledge that the information can be ascribed to the maternal or paternal chromosome.

The DNA may be prepared for analysis by any suitable method known to the skilled artisan, including by PCR using appropriate primers. Where it is desired to analyze the entire genome, the method of whole genome amplification (WGA) may be used. For example, anaphase cells may be transacted enabling visualisation of the two haplomes, after which WGA could be implemented. Commercial kits are readily available for this method including the GenoPlex® Complete WGA kit manufactured by Sigma-Aldrich Corp (St Louis, Mo., USA). This kit is based upon random fragmentation of the genome into a series templates. The resulting shorter DNA strands generate a library of DNA fragments with defined 3 primed and 5 primed termini. The library is replicated using a linear, isothermal amplification in the initial stages, followed by a limited round of geometric (PCR) amplifications.

Numerous strategies are available for PCR amplification of DNA. These include the method described by Klein et al (PNAS 96(8):4494-4499, Apr. 13, 1999) which provides (1) complete, unbiased, whole genome amplification, and (2) the prospect of being able to amplify tens to hundreds of loci.

mRNA samples are also often subject to amplification. In this case amplification is typically preceded by reverse transcription. Amplification of all expressed mRNA can be performed as described in WO 96/14839 and WO 97/01603. Amplification of an RNA sample from a diploid sample can generate two species of target molecule if the subject from whom the sample was obtained is heterozygous at a polymorphic site occurring within expressed mRNA.

A convenient method of identifying nucleotide polymorphisms is by use of microarray technology. An exemplary embodiment of this form of the invention is found in the GeneChip® technology marketed by Affymetrix®. This technology relies on a photolithographic process by coating a 5"×5" quartz wafer with a light-sensitive chemical compound that prevents coupling between the wafer and the first nucleotide of the DNA probe being created. Lithographic masks are used to either block or transmit light onto specific locations of the wafer surface. The surface is then flooded with a solution containing either adenine, thymine, cytosine, or guanine, and coupling occurs only in those regions on the glass that have been deprotected through illumination. The coupled nucleotide also bears a light-sensitive protecting group, so the cycle can be repeated. Other methods of immobilizing probes are provided by a number of companies including Oxford Gene Technology (Oxford, U.K.), Agilent Technologies (Palo Alto, Calif., U.S.A.) and Nimblegen Systems Inc (Madison, Wis., U.S.A).

It is anticipated that probes designed to provide in formation for both haplotypes of a subject may be incorporated onto a single microarray chip. The probes responsible for providing haplotype information derived paternally may be labelled with one type of fluorescent tag, while haplotype information derived maternally could be labelled with a different tag.

In one form of the invention the two or more polymorphisms are part of a coding sequence allele. The present methods may be used to show an association between a gene and a trait by the demonstration of excess allele sharing. In the context of the present invention the term "allele" is used to refer to a genetic variation associated with a coding region and includes an alternative form of a given gene. As used herein the term "allele sharing" refers to the concept of an allele of a gene being present (or shared) in a group of individuals. The presence and extent of allele sharing can be found using any one of a number of statistical software packages available to skilled person. The use of coding sequence alleles is distinct from the HapMap use of non-coding sequence variants (e.g. SNPs and STRs) for indirect indication of coding haplotypes. This indirect approach by HapMap has inherent uncertainty of SNP representativeness of population haplotype diversity, haplotype block length, linkage disequilibrium and phase.

The present methods also reveal a hitherto unknown level of complexity in regards to alleles. As discussed elsewhere herein, the phase of any two regions of a chromosome is important given that recombination events can assort the regions such that any two regions may be present in cis or in trans. Thus, the Applicant predicts the existence of trans alleles whereby the allele present on a chromosome is actually a hybrid allele with one region contributed by the father, and another region contributed by the mother. The existence of such trans alleles has not yet been recognised in the art, and may provide an insight into the generation of alleles or lead to the discovery of new alleles, or methods of predicting new alleles.

The importance of phase also extends to the gene regulatory regions (i.e 5' upstream and 3' downstream sequences). It can be predicted that recombination events will lead to the juxtaposition of a 5' regulatory region from one parent with the 3" regulatory region from the other. The practical result of this re-assorting of regulatory regions could be that expression of the gene under control of those regions is significantly affected.

In another aspect the present invention provides for the selective analysis of paternally-derived DNA and maternally-derived DNA for determining a definitive haplotype of a subject.

In another aspect the present invention provides a method for identifying a gene involved in a multigenic disease or trait, the method including use of a method described herein. Given the present methods for haplotyping based on inference it is very difficult if not impossible to fully investigate the role of any given gene in a multi-genic disease or trait. The provision of a definitive haplotype as described herein removes uncertainties that confound elucidation of the involvement of a single gene in a multi-genic system.

It will be apparent to the skilled artisan that the present invention will have many uses. In one embodiment, the present invention provides use of the methods described herein for identifying a gene involved in a monogenic disease or phenotype. A further embodiment provides use of the methods described herein for identifying a gene involved in a multigenic disease or phenotype. The provision of a definitive haplotype will also allow for closer matching of donor and recipients in tissue transplantation.

The present invention can be applied to any subject. The subject may be human, equine, bovine, caprine, ovine, canine, feline, or porcine. The skilled person will understand that organism such as plants will also be suitable. Some organisms are polyploid (e.g. some plants and shellfish) and the present invention is expected to have even greater advantages given the confounding issues involved whereby three or more homologous chromosomes are present per cell.

In a further aspect the present invention provides use of the methods described herein in identifying genes involved in a drug response. Pharmacogenomics is the study of how an individual's genetic inheritance affects the body's response to drugs. The basis of pharmacogenomics is that drugs may be tailor-made for individuals being adapted to their own genetic makeup. Environment, diet, age, lifestyle, and state of health can all influence a person's response to medicines, but understanding an individual's genetic makeup is considered to be the key to creating personalized drugs with greater efficacy and safety.

Using the present invention it may be possible to create drugs based on the proteins, enzymes, and RNA molecules associated with genes and diseases. This will facilitate drug discovery and allow researchers to produce a therapy more targeted to specific diseases. This accuracy not only will maximize therapeutic effects but also decrease damage to nearby healthy cells.

Instead of the standard trial-and-error method of matching patients with the right drugs, clinicians will be able to analyze a patient's genetic profile and prescribe the best available drug therapy from the beginning of therapy. Not only will this take the guesswork out of identifying the correct drug for the patient, it will speed recovery time and increase safety as the likelihood of adverse reactions may be eliminated. Pharmacogenomics has the potential to dramatically reduce the estimated 100,000 deaths and 2 million hospitalizations that occur each year in the United States as the result of adverse drug response.

One result of implementing the present invention may be more accurate methods of determining appropriate drug dosages. Current methods of basing dosages on weight and age will be replaced with dosages based on patient genetics. An accurate genetic profile could, for example, provide an indication of how well the body metabolises the drug and therefore the time taken to metabolize it. This will maximize the therapy's value and decrease the likelihood of overdose.

Another result of implementing the present invention may be improved methods of screening for disease. Knowing the genetic profile of an individual could identify one or more disease susceptibilities. Knowledge of the susceptibility could allow a person to make adequate lifestyle and environmental changes at an early age so as to avoid or lessen the severity of a genetic disease. Likewise, advance knowledge of a particular disease susceptibility will allow careful monitoring of the individual, and treatments can be introduced at the most appropriate stage to optimize therapy.

A further result of implementing the present invention may be improved vaccines. Vaccines made of genetic material, either DNA or RNA, promise the benefits of existing vaccines without all the risks. Genetic vaccines will activate the immune system but will be unable to cause infections. They will be inexpensive, stable, easy to store, and capable of being engineered to carry several strains of a pathogen simultaneously.

The present invention may also be used to improve the drug discovery and approval process. Pharmaceutical companies will be able to discover potential therapies more easily using genome targets. Previously failed drug candidates may be revived as they are matched with the niche population they serve. The drug approval process should be facilitated as trials are targeted for specific genetic population groups providing greater degrees of success. The cost and risk of clinical trials will be reduced by targeting only those persons capable of responding to a drug.

Thus, the provision of accurate genetic information by the present invention may lead to decreases in the number of adverse drug reactions, the number of failed drug trials, the time it takes to achieve regulatory approval for a drug, the length of time a patient is on medication, the number of medications a patient must take to identify an effective therapy, the effects of a disease on the body (through early detection), and an increase in the range of possible drug targets. These advantages may lead to a net decrease in the cost of health care.

As discussed supra, the methods of the present invention may also be useful in identifying gene or genes that render an individual susceptible to a disease. This is especially the case for multi-genic diseases such as diabetes. For example, a major diabetes susceptibility gene has discovered that could make people with defective copies three times more likely to develop type 2 diabetes. It is known that SNPs in the gene for calpain-10 (a protease) are associated with type 2 diabetes. The association was demonstrated in Mexican Americans, who are susceptible to the disease. Sequencing DNA samples from this population and performing statistical analysis on the sequences, it was found that these Mexican Americans had insulin resistance and showed reduced levels of calpain-10 gene expression. The present invention will allow more simple detection of gene/disease associations, and will facilitate identification of the genetic basis for other genetically complex disorders such as asthma, schizophrenia and Alzheimer's disease.

In another aspect the present invention provides use of the methods for identifying gene targets (or protein targets) for drugs or gene therapy. Knowledge of the genetic basis of disease obtained by practicing the present invention will provide valid targets for drug design and gene therapy. For example, if a gene or genes are identified as having an association with a disease, the activity of that gene could be inhibited or enhanced to provide a therapeutic outcome. Alternatively, the protein product of that gene could form the basis of a screening assay for entities that can bind and modulate the activity of the protein. Furthermore, rational drug design could be instigated if the three dimensional structure of the protein is able to be generated.

In another aspect the present invention provides use of the methods described herein for identifying individuals with a predisposition to a disease. Once a gene is identified as having an association with a particular disease using the present methods the skilled person will be able to design an assay to screen for the defective form of the gene. Identification of persons at risk of certain diseases will allow preventative measures such as drug therapy and lifestyle changes to be instigated.

In a further aspect the present invention provides use of the methods to identify individuals with a predisposition to a response to an environmental stimulus. An example of this use could be to identify persons with allergies to various substances. In some individuals, the response to allergens (eg in peanuts or bee venom) can lead to a potentially fatal anaphylactic reaction. Identification of especially sensitive individuals would allow the instigation of desensitization procedures.

Finally, it is to be understood that various other modifications and/or alterations may be made without departing from the spirit of the present invention as outlined herein.

Future patent applications may be filed in Australia or overseas on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention or inventions.

The invention claimed is:

1. An in situ method for obtaining genetic information from a biological sample, wherein said biological sample contains a plurality of condensed metaphase chromosomes or fragments thereof obtained from a diploid cell, and wherein the method comprises the steps of:
   a) hybridising a plurality of allele-specific probes to the plurality of condensed metaphase chromosomes or fragments thereof;
   b) identifying whether any two allele-specific probes are bound in cis on one chromosome, or in trans across two sister chromosomes, such that the phase of any two allele-specific probes can be determined; and
   c) obtaining genetic information from the phase of any two allele-specific probes;
   whereby the genetic information obtained is nucleotide sequence information.

2. The method according to claim 1, wherein the plurality of condensed metaphase chromosomes or fragments thereof are obtained from a somatic cell.

3. The method according to claim 1, wherein at least one of the plurality of allele-specific probes comprises a single nucleotide polymorphism.

4. The method according to claim 3, wherein at least one of the plurality of allele-specific probes detects the presence of a single nucleotide polymorphism.

5. The method according to claim 1, wherein the nucleotide sequence information provides allelic information.

6. The method according to claim 5, wherein the allelic information relates to a coding region allele.

7. The method according to claim 6, wherein the biological sample is obtained from a subject and wherein the genetic information is capable of providing phenotypic information for the subject.

8. The method according to claim 7, wherein the phenotypic information is selected from the group consisting of the presence or absence of a disease, condition, or disorder; a predisposition to a disease, condition, or disorder; the ability or inability to respond to a potentially therapeutic molecule; the ability or inability to mount an immune response against a foreign antigen or a self-antigen; the presence or absence of an allergy; and a predisposition to an allergy.

* * * * *